United States Patent [19]
Lin et al.

[11] Patent Number: 6,035,691
[45] Date of Patent: Mar. 14, 2000

[54] ADJUSTABLE ROD BENDING DEVICE FOR A CORRECTIVE SPINAL ROD WHICH IS USED IN A SURGICAL OPERATION

[76] Inventors: Ruey-Mo Lin, A6-3, No. 61 Hsiao-Tung Rd.; Rong-Shean Lee, 4 Fl., No. 45, Lane 120, Tung-Ning Rd., both of Tainan, Taiwan; Ying-Ming Huang, No. 2-1, Lane 22, Tai-Tang 1st St., Pingtung City, Taiwan

[21] Appl. No.: 09/371,232

[22] Filed: Aug. 10, 1999

[51] Int. Cl.[7] ............................................. B21D 37/02
[52] U.S. Cl. ............................ 72/413; 72/212; 72/308
[58] Field of Search ........................... 72/212, 213, 413, 72/387, 388, 381

[56] References Cited

U.S. PATENT DOCUMENTS

| | | | |
|---|---|---|---|
| 483,094 | 9/1892 | Ansted | 72/413 |
| 1,118,046 | 11/1914 | Poffinbarger | 72/413 |
| 1,295,542 | 2/1919 | McIntire | 72/413 |
| 1,640,827 | 8/1927 | Frater | 72/413 |
| 1,826,783 | 10/1931 | Hess | 72/413 |
| 1,830,647 | 11/1931 | Engel | 72/413 |
| 2,783,815 | 3/1957 | Tegarden | 72/413 |
| 5,123,272 | 6/1992 | Heaman | 72/413 |
| 5,187,969 | 2/1993 | Morita | 72/413 |
| 5,224,370 | 7/1993 | Morita | 72/413 |
| 5,477,724 | 12/1995 | Velan et al. | 72/213 |
| 5,490,409 | 2/1996 | Weber | 72/458 |
| 5,546,784 | 8/1996 | Haas et al. | 72/413 |
| 5,557,964 | 9/1996 | Jessop et al. | 72/413 |

FOREIGN PATENT DOCUMENTS

| | | | |
|---|---|---|---|
| 1-95829 | 4/1989 | Japan | 72/413 |
| 1-133622 | 5/1989 | Japan | 72/413 |

*Primary Examiner*—David Jones
*Attorney, Agent, or Firm*—Jackson Walker L.L.P.

[57] ABSTRACT

An adjustable rod bending device includes a support table, a pivot base mounted on the support table, a pivot bracket pivotally mounted on the pivot base, and multiple juxtaposed rollers mounted in the pivot bracket to pivot therewith and each having an upper end adjustably mounted in the pivot bracket and a lower end formed with an arcuate pressing surface. The arcuate pressing surface of each of the rollers can be moved to press a corrective spinal rod supported by two support posts, thereby accurately bending the corrective spinal rod.

11 Claims, 6 Drawing Sheets

ADJUSTABLE ROD BENDING DEVICE FOR A CORRECTIVE SPINAL ROD WHICH IS USED IN A SURGICAL OPERATION

CROSS-REFERENCES TO RELATED APPLICATIONS

Not Applicable.

BACKGROUND OF THE INVENTION

1. Field of the Invention

The present invention relates to an adjustable rod bending device, and more particularly to an adjustable rod bending device for bending a corrective spinal rod which is used in a surgical operation.

2. Description of the Related Art

A rod bender is used for bending a corrective spinal rod that can be used in a surgical operation for correcting the lumbar curvatures of the human body.

The closest prior art of which the applicant is aware is disclosed in U.S. Pat. No. 5,490,409, entitled "Adjustable Cam Action Rod Bender for Surgical Rods". However, the user has to exert a great force on the bender with two hands to bend the metallic rod, thereby causing inconvenience to the user. In addition, the metallic rod is locally bent to form an arc such that it has to fit a required curve by multiple small arcs whereby the curvature of the corrective spinal rod is determined based on the doctor's experience, such that when the doctor does not have efficient experience, the curvature of the corrective spinal rod is often not satisfactory such that he has to repeat the operations again and again, thereby decreasing the accuracy of bending the corrective spinal rod and probably yielding the material.

A second conventional rod bender in accordance with the prior art includes two elongated plates each containing a hole defined in one distal end whereby the corrective spinal rod has its two ends inserted into the hole of each of the two elongated plates. The two plates are then turned in opposite directions relative to each other, thereby bending the corrective spinal rod. However, the user has to exert a great force on the bender with two hands so as to bend the metallic rod, thereby causing inconvenience to the user. In addition, it is not easy to control the direction of force exerted on the two plates during the bending process, thereby greatly decreasing the accuracy of bending the corrective spinal rod. Further, the curvature of the corrective spinal rod is determined based on the doctor's experience, thereby decreasing the accuracy of bending the corrective spinal rod.

Other prior arts of which the applicant is aware are disclosed in U.S. Pat. No. 4,141,235, entitled "Hydraulic Bending Machine", U.S. Pat. No. 4,132,100, entitled "Hand-Operated Tool For Bending Pipes", U.S. Pat. No. 3,987,656, entitled "Pipe Bending Apparatus", and U.S. Pat. No. 4,910,984, entitled "Progressive Roller Bender", wherein the mentioned devices are used in non-medical applications.

The present invention has arisen to mitigate and/or obviate the disadvantage of the conventional rod bender.

BRIEF SUMMARY OF THE INVENTION

In accordance with one aspect of the present invention, an adjustable rod bending device comprises a support table; a pivot base mounted on the support table; a pivot bracket pivotally mounted on the pivot base; and multiple juxtaposed rollers mounted in the pivot bracket to pivot therewith and each having an upper end adjustably mounted in the pivot bracket and a lower end formed with an arcuate pressing surface. Each of the rollers includes a scale thereon.

The pivot bracket includes a bottom board pivotally mounted on the pivot base and containing an elongated groove to receive the rollers therein, two side plates each extending from the bottom board, and a support beam separated from the bottom board and mounted between the two side plates. The support beam contains multiple threaded bores, and the adjustable rod bending device comprises multiple threaded rods each extending through one of the threaded bores, and each having a lower end attached to the upper end of one of the rollers to move the respective roller, an adjusting bolt extending through one of the two side plates and abutting the outermost roller, a fixed tube secured on the side plate and receiving the adjusting bolt therein, and a handle having a distal end detachably mounted in the fixed tube.

The upper end of each of the rollers contains an inverted T-shaped guide groove having a bottom channel and a top channel having a dimension smaller than that of the bottom channel, and each of the threaded rods includes a stub extending from the lower end thereof to rotate therewith and slidably received in the top channel, and a ring extending from the stub to rotate therewith and slidably received in the bottom channel.

The adjustable rod bending device comprises two support posts each mounted on the support table and each containing a notch, a corrective spinal rod located under the arcuate press surface of each of the rollers and having two ends each received in the notch of the two support posts, and a U-shaped support bracket mounted on one of the two support posts to receive the bottom board of the pivot bracket therein. The notch is used to tightly retain the spinal rod.

The support table contains an elongated guide slot, each of the two support posts is slidably received in the guide slot and includes a retaining block mounted on the lower end thereof and abutting the bottom of the support table, and the adjustable rod bending device comprises two washers each mounted on the top of the support table and each located beside the support post, and two locking bolts each extending through the washer and screwed in the retaining block.

Further benefits and advantages of the present invention will become apparent after a careful reading of the detailed description with appropriate reference to the accompanying drawings.

DETAILED DESCRIPTION OF THE INVENTION

Figure 1:
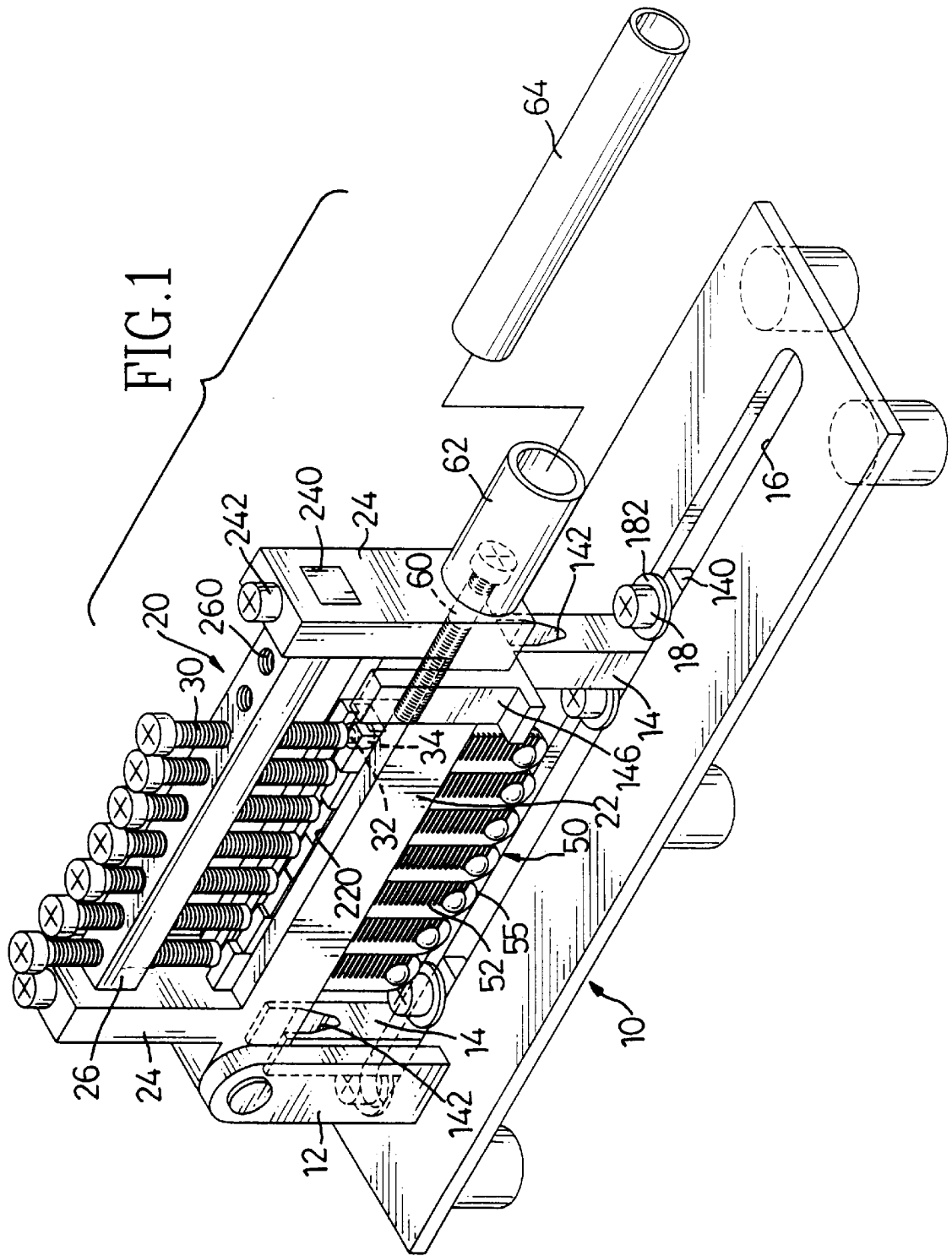
FIG. 1 is a perspective view of an adjustable rod bending device for a corrective spinal rod in accordance with the present invention.

Lumbar lordosis appears in children. Trauma, inflammation and degeneration could change its contour. Aging is the main influencing factor for the adults. Loss of lordosis necessitates spinal fusion. Many efforts have been taken to return the lumbar lordosis to preoperative standing conditions. In practice, it has to bend a corrective metallic rod which is then imbedded in the human body so as to fix the spine. The curvature of the bent corrective rod is determined by the doctor. The objective of the present invention is to determine the curvature of the corrective rod to be bent so as to overcome the shortcomings of the prior art references.

A new rod bender was designed, which has several rollers to fit the curvature and to bend the rod by rotary motion. It is not only effort-saving but also makes the contour of the spinal rod smoother.

In the present invention, analytic and simulation solutions are used to control the springback of the spinal rod during bending. It confirmed that the analytical solutions were accurate enough to estimate the springback. Consequently analytical solutions are used instead of simulations.

The doctor in the spinal surgery clinic can use the radiographs and the rod bending device developed in accordance with the present invention to construct the corrective spinal rod more easily and accurately.

Referring to the drawings and initially to FIGS. 1–4, an adjustable rod bending device in accordance with the present invention is used to bend a corrective spinal rod to be used in a surgical operation for correcting the lumbar lordosis curvature of the human body.

Figure 2:
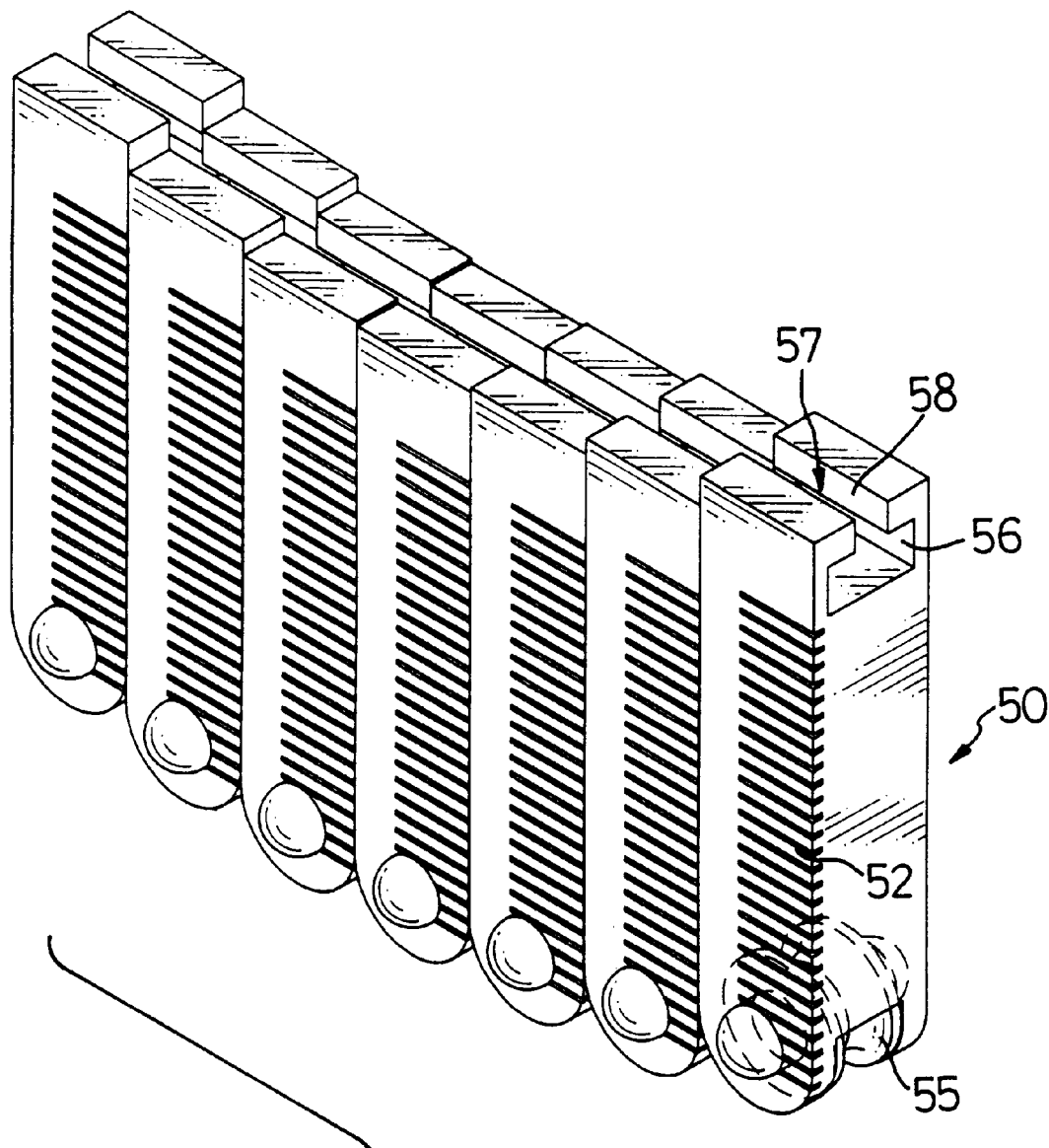
FIG. 2 is a perspective view of the rollers of the adjustable rod bending device in FIG. 1.
Figure 5:
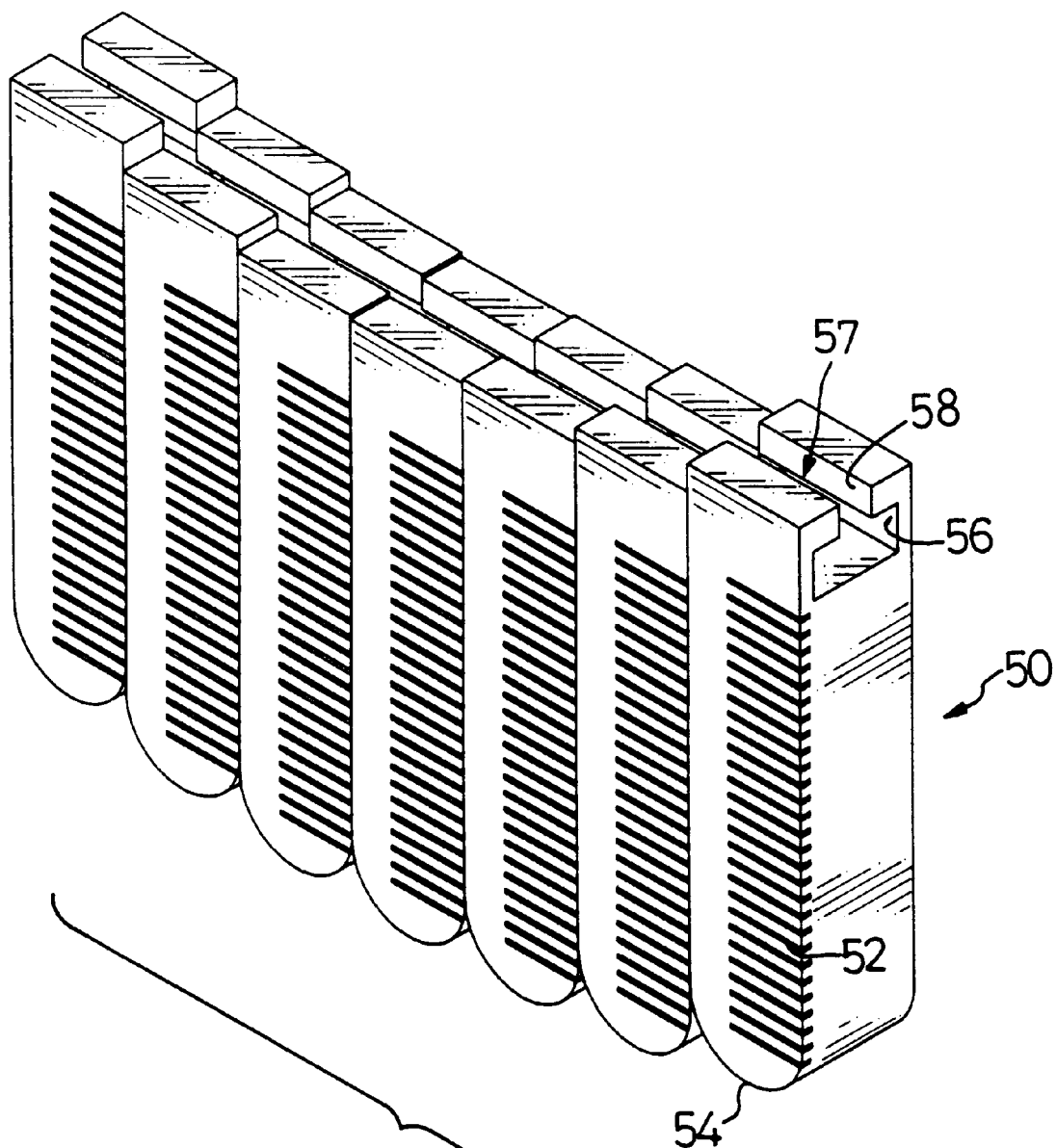
FIG. 5 is a perspective view of the rollers of the adjustable rod bending device in accordance with another embodiment of the present invention.

The adjustable rod bending device comprises a support table (10), a pivot base (12) secured on the support table (10), a pivot bracket (20) pivotally mounted on the pivot base (12), and multiple juxtaposed rollers (50) each mounted in the pivot bracket (20) to pivot therewith and each having an upper end adjustably mounted in the pivot bracket (20) and a lower end formed with a wheel (55) as shown in FIG. 2 or an arcuate pressing surface (54) as shown in FIG. 5. Each of the rollers includes a scale (52) bonded or etched thereon.

The pivot bracket (20) includes a bottom board (22) pivotally mounted on the pivot base (12) and containing an elongated groove (220) to receive each of the rollers (50) therein, two side plates (24) each extending from the bottom board (22), and a support beam (26) separated from the bottom board (22) and mounted between the two side plates (24). The support beam (26) contains multiple threaded bores (260), and the adjustable rod bending device comprises multiple threaded rods (30) each extending through one of the threaded bores (260) and each having a lower end attached to the upper end of one of the rollers (50) to linearly move the respective roller (50) up and down.

Each of the two side plates (24) contains a hole (240) to receive the support beam (26), and two locking screws (242) each extending through the side plate (24) and pressing the support beam (26). When each of the threaded rods (30) is detached from the support beam (26), the locking screw (242) is screwed from the side plate (24) so that the Support beam (26) can be removed from the side plate (24) through the hole (240) to be replaced by a second support beam (26). The number of the threaded bore (260) of the second support beam (26) can be increased to increase the number of the threaded rod (30) and the roller (50) whereby the contact area between the wheel (55) of the roller (50) and the corrective spinal rod (66) is decreased, thereby increasing the precision of the curvature of the corrective spinal rod (66).

The upper end of each of the rollers (50) contains an inverted T-shaped guide groove (57) having a bottom channel (56) and a top channel (58) having a width smaller than that of the bottom channel (56), and each of the threaded rods (30) includes a stub (32) extending from the lower end thereof to rotate therewith and be slidably received in the top channel (58), and a ring (34) extending from the stub (32) to rotate therewith and be slidably received in the bottom channel (56).

The adjustable rod bending device comprises an adjusting bolt (60) extending through one of the two side plates (24) and abutting the outermost roller (50) to retain and lock the rollers (50), thereby preventing the rollers (50) from deviating from their positions. The adjusting bolt (60) can be turned from the side plate (24) by a screwdriver (not shown), thereby releasing the rollers (50) so as to increase or decrease the number of the rollers (50).

The adjustable rod bending device also comprises a fixed tube (62) secured on the side plate (24) and receiving the adjusting bolt (60) therein, and a handle (64) having one end detachably mounted in the fixed tube (62).

The adjustable rod bending device comprises two support posts (14) each mounted on the support table (10) and each containing a V-shaped notch (142), a corrective spinal rod (66) located under the wheel (55) or the arcuate pressing surface (54) of each of the rollers (50) and having two ends each received in the V-shaped notch (142) of the two support posts (14), and a U-shaped support bracket (146) mounted on one of the two support posts (14) to detachably receive the bottom board (22) of the pivot bracket (20) therein. The arcuate pressing surface (54) of each of the rollers (50) can be moved to press the corrective spinal rod (66) supported by the two support posts (14), thereby accurately bending the corrective spinal rod (66). The notch (142) is used to retain the corrective spinal rod (66), and is suitable for corrective spinal rods (66) of different diameters.

The support table (10) contains an elongated guide slot (16), each of the two support posts (14) is slidably received in the guide slot (16) and includes a retaining block (140) mounted on the lower end thereof and abutting the bottom of the support table (10), and the adjustable rod bending device comprises two washers (182) each mounted on the top of the support table (10) and each located beside the support post (14), and two locking bolts (18) each extending through a washer (182) and screwed into the retaining block (140).

Figure 3:
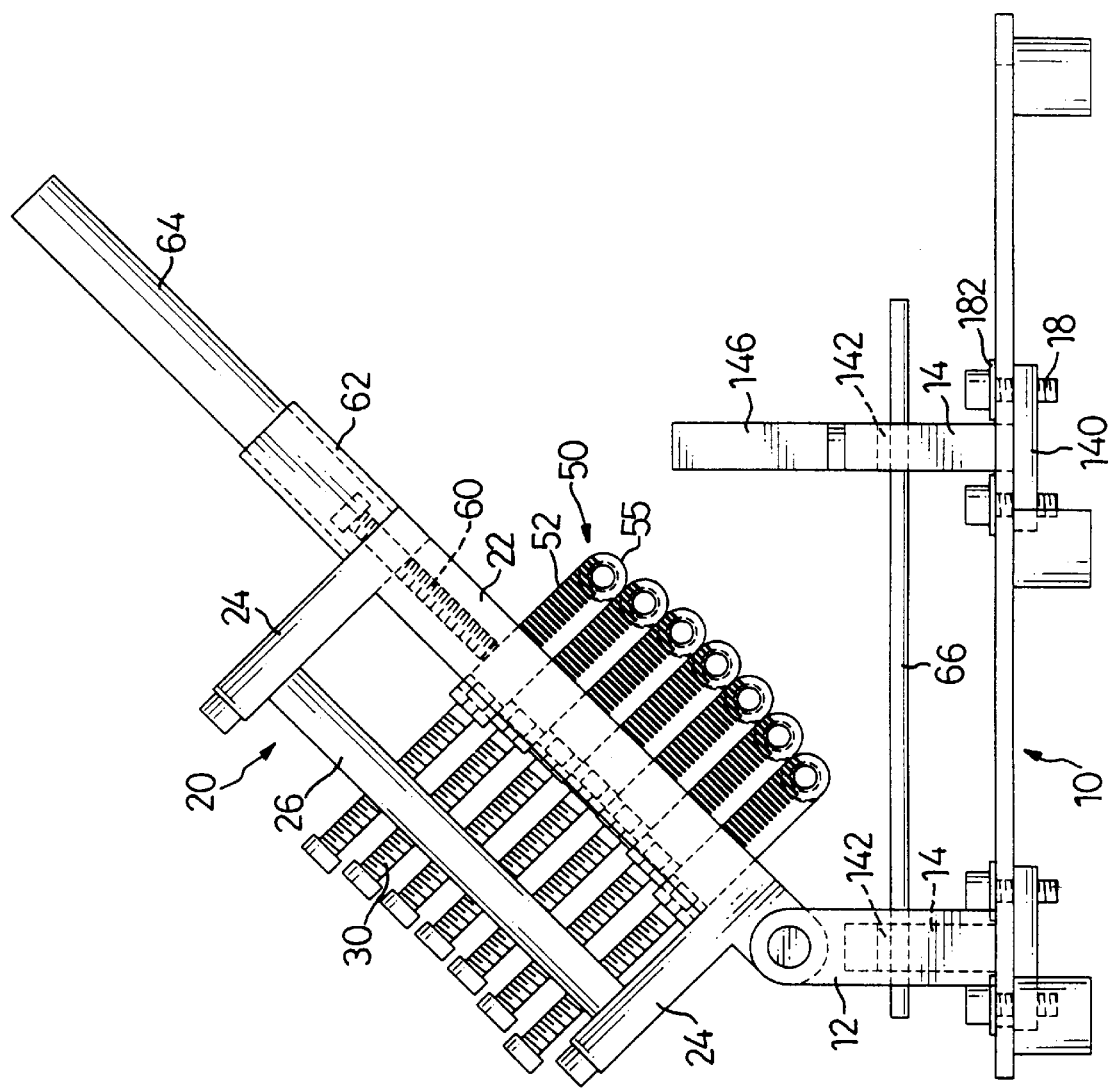
FIG. 3 is a front plan view of the adjustable rod bending device in FIG. 1.
Figure 4:
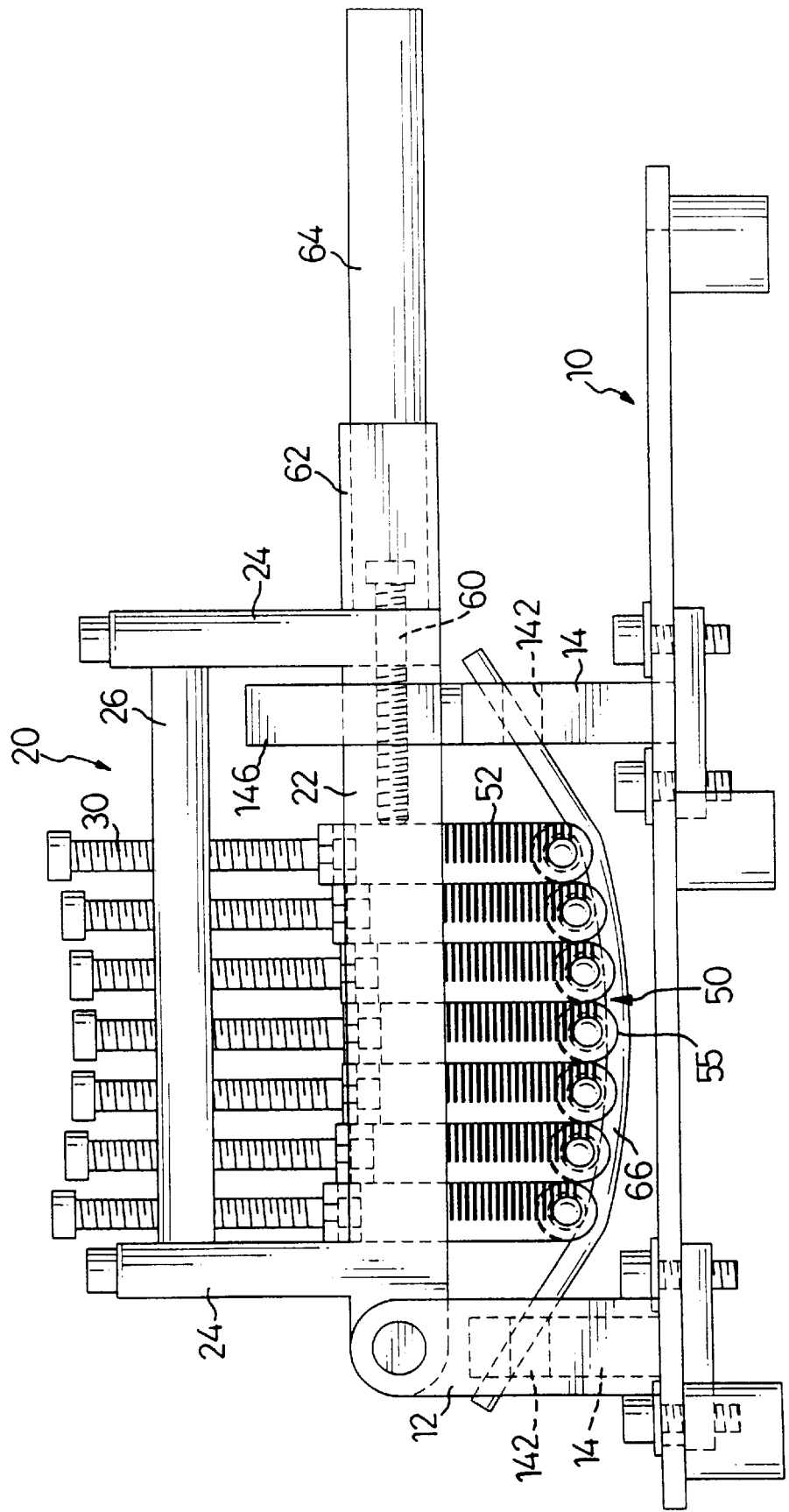
FIG. 4 is an operational view of the adjustable rod bending device in FIG. 1.

In operation, referring to FIGS. 3 and 4 with reference to FIGS. 1, each of the threaded rods (30) is rotated on the support beam (26) so as to linearly move the respective roller (50) such that the wheels (55) or the arcuate pressing surfaces (54) of the rollers (50) form a curve. The pivot bracket (20) is then pivoted relative to the support table (10) by pushing the handle (64) so as to move the rollers (50) from the position as shown in FIG. 3 to the position as shown in FIG. 4 where the wheels (55) or the arcuate pressing surfaces (54) of the rollers (50) press the corrective spinal rod (66), thereby bending the corrective spinal rod (66). The scale (52) of each of the rollers (50) can be used to indicate the location of each of the rollers (50) whereby the wheels (55) or the pressing surfaces (54) of the rollers (50) forms a curve whose curvature mates with that of the curve of the corrective spinal rod (66) so as to accurately simulate the curve of the corrective spinal rod (66) to be bent. The scale (52) of each of the rollers (50) is determined by a computer.

The corrective spinal rod (66) is usually made of elastic material such as a titanium alloy, stainless steel and the like. The springback distance of the elastic corrective spinal rod

(66) is compensated whereby curvature of the corrective spinal rod (66) is the actual curvature which is required to correct the lumbar lordosis.

Referring to FIGS. 2 and 5, each of the rollers (50) includes a wheel (55) or an arcuate surface (54) mounted or formed on the lower end thereof to press the corrective spinal rod (66) for bending the corrective spinal rod (66).

Figure 6:
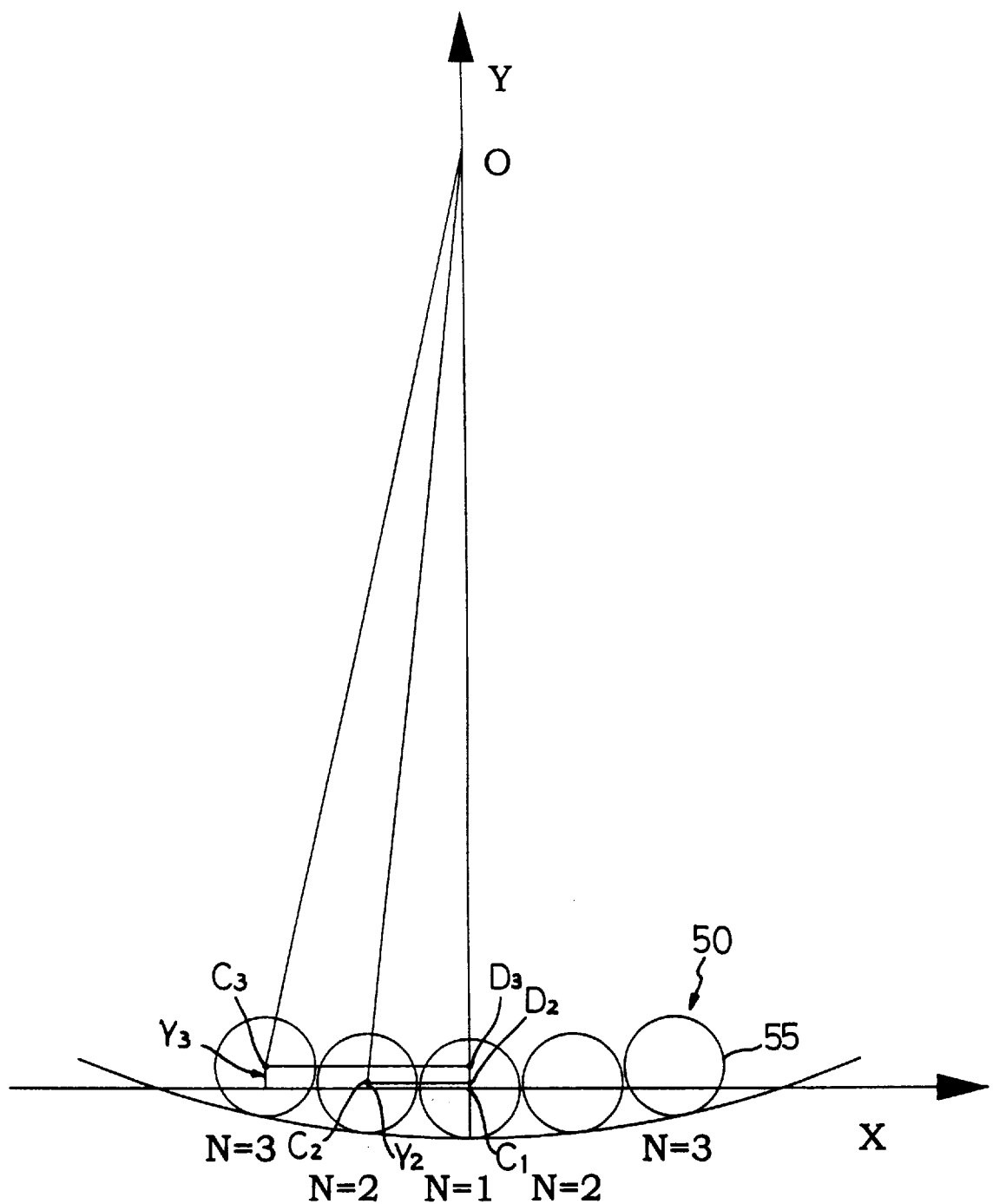
FIG. 6 is a schematic view showing how to determine the location of the rollers of the rod bending device as shown in FIG. 1.

Referring to FIG. 6 with reference to FIGS. 1–3, a plurality of rollers (50) are juxtaposed to with each other, wherein, N is the number of the rollers (50), $r_{roller}$ is the radius of the wheel (55) or the arcuate surface (54) of each of the rollers (50), $r_{design}$ is the curvature of the corrective spinal rod (66) to be bent, $OC_1$ is the distance between the center (O) of the designed curvature and the center (C1) of the first roller where N=1, and $Y_n$ is the distance between the center of the Nth roller and the X axis. Then, the value of the distance of $Y_n$ is determined by the following equation:

$$Y_n = OC_1 - \{(r_{design} - r_{roller})^2 - [2(N-1)r_{roller}]^2\}^{1/2}$$

In such a manner, the location of each of the rollers (50) can be determined.

It should be clear to those skilled in the art that further embodiments may be made without departing from the scope of the present invention.

What is claimed is:

1. An adjustable rod bending device comprising:

a support table (10);

a pivot bracket (20) pivotally mounted on said support table (10); and multiple juxtaposed rollers (50) mounted in said pivot bracket (20) to pivot therewith and each having an upper end adjustably mounted in said pivot bracket (20) and a lower end formed with an arcuate pressing surface (54).

2. The adjustable rod bending device in accordance with claim 1, further comprising a pivot base (12) mounted on said support table (10), wherein said pivot bracket (20) includes a bottom board (22) pivotally mounted on said pivot base (12) and containing an elongated groove (220) to receive said rollers (50) therein, two side plates (24) each extending from said bottom board (22), and a support beam (26) separated from said bottom board (22) and mounted between said two side plates (24).

3. The adjustable rod bending device in accordance with claim 2, wherein said support beam (26) contains multiple threaded bores (260), and said adjustable rod bending device further comprises multiple threaded rods (30) each extending through one of said threaded bores (260), and each having a lower end attached to the upper end of one of said rollers (50) to move said the respective roller (50).

4. The adjustable rod bending device in accordance with claim 3, wherein said upper end of each of said rollers (50) contains an inverted T-shape guide groove (57) having a bottom channel (56) and a top channel (58) having a width smaller than that of said bottom channel (56), and each of said threaded rods (30) includes a stub (32) extending from the lower end thereof to rotate therewith and be slidably received in said top channel (58), and a ring (34) extending from said stub (32) to rotate therewith and be slidably received in said bottom channel (56).

5. The adjustable rod bending device in accordance with claim 2, further comprising an adjusting bolt (60) extending through one of said two side plates (24) and abutting the outermost roller (50).

6. The adjustable rod bending device in accordance with claim 5, further comprising a fixed tube (62) secured on said side plate (24) and receiving said adjusting bolt (60) therein, and a handle (64) having one end detachably mounted in said fixed tube (62).

7. The adjustable rod bending device in accordance with claim 2, further comprising two support posts (14) each mounted on said support table (10) and each containing a V-shaped notch (142), and a corrective spinal rod (66) located under said arcuate pressing surface (54) of each of said rollers (50) and having two ends each received in said V-shaped notch (142) of said two support posts (14).

8. The adjustable rod bending device in accordance with claim 7, further comprising a U-shaped support bracket (146) mounted on one of said two support posts (14) to receive said bottom board (22) of said pivot bracket (20) therein.

9. The adjustable rod bending device in accordance with claim 1, wherein said support table (10) contains an elongated guide slot (16), each of said two support posts (14) is slidably received in said guide slot (16) and includes a retaining block (140) mounted on the lower end thereof and abutting the bottom of said support table (10), and said adjustable rod bending device further comprises two washers (182) each mounted on the top of said support table (10) and each located beside said support post (14), and two locking bolts (18) each extending through said washer (182) and screwed in said retaining block (140).

10. The adjustable rod bending device in accordance with claim 1, wherein each of said rollers includes a scale (52) mounted thereon.

11. The adjustable rod bending device in accordance with claim 1, wherein each of said rollers (50) includes a wheel (55) mounted on the lower end thereof.

* * * * *